United States Patent [19]

Zupan

[11] 4,440,777

[45] Apr. 3, 1984

[54] USE OF EUCALYPTOL FOR ENHANCING SKIN PERMEATION OF BIO-AFFECTING AGENTS

[75] Inventor: Jacob A. Zupan, St. Joseph, Mo.

[73] Assignee: Merck & Co., Inc., Rahway, N.J.

[21] Appl. No.: 280,967

[22] Filed: Jul. 7, 1981

[51] Int. Cl.³ .................... A61K 31/19; A61K 31/40
[52] U.S. Cl. .................................. 424/274; 424/45;
424/59; 424/227; 424/230; 424/238; 424/244;
424/258; 424/273 R; 424/278; 424/279;
424/310; 424/315; 424/316; 424/317
[58] Field of Search ............... 424/274, 317, 278, 45

[56] References Cited

U.S. PATENT DOCUMENTS 3,472,931 10/1969 Stonghton ........................... 424/180
3,527,864 9/1970 MacMillan et al. ................ 424/177

OTHER PUBLICATIONS

Chem. Abst., vol. 94 (1981), 145378e.
Merck Index, 9th Ed. ©1976, 520, 649, 656657,834 1164.
Proceedings of Joint Conf. on Cosmetic Sciences, 1968, pp. 189–203, Robert J. Feldmann & Howard I. Maibach.
The Extra Pharmacopoeia, Martindale, pp. 1461–1463, 27th Edition, 1977.

*Primary Examiner*—Stanley J. Friedman
*Attorney, Agent, or Firm*—Manfred Polk; Michael C. Sudol, Jr.; Mario A. Monaco

[57] ABSTRACT

Greatly enhanced delivery of a wide variety of bio-affecting agents is provided by formulations for topical application comprising at least one bio-affecting agent and eucalyptol. Optionally, the formulation can further comprise a non-toxic topical carrier and/or an additional penetration enhancer. The eucalyptol acts as a unique transport agent which readily delivers the active bio-affecting agent across the stratum corneum to the target area. Cosmetic and therapeutic dermatological agents as well as systemically effective therapeutic agents can be easily formulated with eucalyptol and effectively delivered through the skin to the desired site, i.e., to the underlying tissues of the epidermis and dermis or to the general circulation.

11 Claims, No Drawings

USE OF EUCALYPTOL FOR ENHANCING SKIN PERMEATION OF BIO-AFFECTING AGENTS

BACKGROUND OF THE INVENTION

1. Field of the Invention

The present invention relates to novel compositions for topical application and delivery of a bio-affecting agent through the protective outer layer of the skin and into the underlying tissues or into the general circulation. More specifically, the invention relates to a composition comprising at least one bio-affecting agent and eucalyptol, and optionally, a nontoxic topical carrier and/or another penetration enhancer.

As used herein, the term "bio-affecting agent" refers to any chemical substance or formulation thereof which beneficially affects the mammalian body. Typically, the bio-affecting agent herein can be a "dermally effective dermatological agent" or a "systemically effective therapeutic agent". The term "dermally effective dermatological agent" as used herein refers to those chemical substances which when applied to mammalian skin exert a beneficial topical effect, which can be of a cosmetic nature (e.g., by protecting the skin against external factors or by improving appearance) or of a therapeutic nature (e.g., by attenuating the severity of a dermal disease). The term "systemically effective therapeutic agent" as used herein refers to those chemical substances which when administered by various routes such as intravenous infusion, intramuscular injection, oral, rectal or buccal routes, enter the general circulation and exhibit a therapeutic effect. The expressions "dermally effective dermatological agent" and "systemically effective therapeutic agent" are not intended to be mutually exclusive, however, it being recognized that a number of bio-affecting agents are indeed effective both dermally and systemically.

2. Description of the Prior Art

Eucalyptol is a well-known chemical compound which has long been used as an inhalational expectorant. It is also known by the names cineole and cajeputal. The art is also well-versed in the preparation of eucalyptol.

The skin of humans and other warm-blooded animals provides an excellent barrier to the penetration of exogenous chemical substances. The outer layer of the epidermis, called the stratum corneum, offers the maximum resistance to penetration, whereas the lower layers are relatively permeable. For proper treatment of dermal conditions, it is important that the active agent penetrate the stratum corneum where it is retained. From this reservoir in the outer layer, the bio-affecting agent is slowly released and penetrates the underlying areas where it exhibits its therapeutic or cosmetic effect. When dermatological agents such as sunscreens, which protect the underlying tissues from external factors (ultraviolet rays) are used, maximum retention in the stratum corneum is essential. On the other hand, the relative permeability of the layers of the epidermis below the stratum corneum can also allow access to the systemic circulation; indeed, it is necessary for the therapeutic agent to penetrate the stratum corneum in order to provide systemic therapeusis from the transdermal route.

It is well-known that the application of various therapeutic and cosmetic agents to the skin is useful for the treatment of a number of dermal conditions, e.g., hydrocortisone for pruritus and erythema in a topic dermatitis, erythromycin or tetracyclines for acne, 5-iodo-2'-deoxyuridine for herpes simplex, 5-fluorouracil for psoriasis and skin cancer, hydroquinone for lightening skin color and p-aminobenzoic acid for blocking the harmful rays of the sun.

It is also well-known that a number of therapeutically active agents, such as $\beta$-blockers, antihypertensives, antiarrhythmics, antianginal agents, vasodilators, antiemetics, antibacterials, antifungals, corticosteroids, progestins, estrogens, androgens and antiinflammatories, when administered to warm-blooded animals by a number of various routes such as by intravenous infusion, intramuscular injection, oral, rectal or buccal routes, enter the general circulation and produce the appropriate systemic therapeutic effect. It is also known that the aforementioned methods of administration have certain disadvantages. For example, the intravenous and intramuscular routes are not only painful for the patient, but also must be performed by a trained individual. Buccal and rectal administration often produce discomfort and annoyances for the patient. Oral administration, although generally acceptable for the patient, often does not deliver the majority of the therapeutic agent to systemic circulation. This diminished drug delivery is usually attributed to poor absorption from the gastrointestinal tract and/or to degradation of the agent by the acidic medium of the stomach, by the enzymes in the gastrointestinal tract and surrounding tissue or by the rapid metabolizing enzymes of the liver through which the drug must pass before it enters the systemic circulation. For example, drugs such as anti-bacterials, narcotic analgesics, $\beta$-blockers and others require relatively high doses when given orally due to the remarkable liver metabolism encountered. Effective delivery of such drugs through the skin would require much lower doses because the so-called "first pass" metabolism would be avoided.

Recognizing the fact that the outer layer of the skin, the epidermis, protects the area under the skin from the penetration of foreign chemicals, many investigators have turned to various enhancing agents, e.g., dimethylsulfoxide, dimethylformamide, methyldecylsulfoxide (U.S. Pat. No. 3,527,864) and dimethylacetamide (U.S. Pat. No. 3,472,931) in order to overcome the aforementioned problems and to deliver topically active agents more efficiently through the skin, as well as to enhance the absorption of systemically active therapeutic agents through the skin and into the general circulation. Dimethylsulfoxide, which is superior to both dimethylformamide and dimethylacetamide, has been shown to enhance the absorption through the skin of hydrocortisone and testosterone (Robert J. Feldmann and Howard I. Maibach, *Proceedings of the Joint Conference on Cosmetic Science* (1968), pages 189–203). Thus, the addition of dimethylsulfoxide to formulations of therapeutically active agents enhances the penetration of said agents through the skin and into the general circulation, thereby overcoming most of the aforementioned problems encountered by other routes of administration. Unfortunately, the use of dimethylsulfoxide is not without problems, for in addition to causing foul taste and body odor, it causes burning and erythema on the skin, activates latent virus infections within cells, reduces the relucency of the lens cortex and produces teratogenicity and tissue necrosis in animals. Compare Martindale, *The Extra Pharmacopoeia*, pages 1461–1463, Twenty-seventh Edition (1977), and the reference cited therein.

Thus, there exists a clear and present need for a novel agent to enhance the absorption through the skin of bio-affecting agents which is devoid of the disadvantages and drawbacks that to date have characterized the prior art enhancing agents.

OBJECTS AND SUMMARY OF THE INVENTION

Accordingly, a major object of the present invention is the provision of a novel agent for enhancing the skin-permeation of bio-affecting agents.

It is also a major object of the present invention to provide a novel agent which will enhance the dermal absorption of dermatological (i.e., therapeutic or cosmetic) agents and which will enhance the delivery through the skin and into the general circulation of systemically active therapeutic agents.

Another object of the invention is to provide an enhancing agent which is devoid of toxic side effects.

Yet another object of the invention is to provide novel compositions utilizing such novel enhancing agents, which formulations are useful for topical application.

Still another object of the present invention is to provide a method for enhancing the skin penetration of bio-affecting chemicals.

Other objects, features and advantages of the invention will be apparent to those skilled in the art upon a study of this disclosure and the appended claims.

It has now been unexpectedly discovered that the aforenoted objects can be achieved by employing eucalyptol as the enhancing agent and by employing same in a composition of matter further comprising at least one bio-affecting agent. The compositions can also further comprise a topical carrier material and/or an additional penetration enhancer. The bio-affecting agent is present in the composition in a biologically effective amount, i.e., in an amount sufficient to produce the desired biological effect. Thus, when the bio-affecting agent is a dermatological agent, it is utilized in a dermally effective amount, i.e., in an amount sufficient to evoke the desired dermal effect (which may be cosmetic or therapeutic in nature). On the other hand, when the bio-affecting agent is a systemically active therapeutic agent and introduction of the agent into the general circulation is desired, then the agent is employed in a systemically effective amount, i.e., in an amount sufficient to produce the desired systemic response. Eucalyptol is employed in the instant compositions in an amount sufficient to enhance skin permeation of the bio-affecting agent.

DETAILED DESCRIPTION OF THE INVENTION

The present invention provides compositions and methods for surprisingly increasing the rate of penetration through the skin of various bio-affecting agents. The amount of dermatological agents absorbed into the underlying tissues of the skin and the amount of systemically effective therapeutic agents absorbed into the general circulation can be dramatically increased utilizing the compositions and methods of the instant invention.

A compositional formulation of the instant invention can simply comprise a stable solution or suspension of the bio-affecting agent in eucalyptol, or it can comprise a combination of the bio-affecting agent and eucalyptol with one or more carrier materials to form a solution, suspension, lotion, cream, ointment, aerosol spray or the like. Any suitable non-toxic or pharmaceutically acceptable topical carrier material or vehicle can be used. Such carrier materials are per se well known to those skilled in the art of topical pharmaceutical formulations. Compare, for example, *Remington's Pharmaceutical Sciences,* 14th Edition (1970). Alternatively, a solution or suspension of the bio-affecting agent and eucalyptol can be incorporated into a polymeric gel or film.

The various bio-affecting agents envisaged by the present invention are conveniently topically administered to warm-blooded animals in combination with eucalyptol in conventional unit dosage amount and form. The formulation comprised of a bio-affecting agent, eucalyptol and, if desired, vehicle(s) and/or additional penetration enhancer, can be applied directly to the skin, or can be applied to a carrier material such as a bandage, which can then be adhered to the skin.

The ratio of eucalyptol to the vehicle generally can vary from about 1:1000 to 100% eucalyptol. Additionally, however, when it is desired to use an additional penetration enhancer, a portion of either the eucalyptol or carrier can be replaced with an equivalent amount of the additional penetration enhancer. Mixtures of eucalyptol and other penetration enhancers, i.e., compounds which enhance the skin penetration of bio-affecting agents, have been found to be particularly useful in providing surprisingly excellent initial diffusion rates and extended periods of time for which such diffusion continues. For example, N,N-diethyl-m-toluamide (DEET), discussed in co-assigned and copending U.S. patent application Ser. Nos. 127,881 and 127,883, both filed Mar. 6, 1980, forms an appropriate mixture with eucalyptol. Examples of other penetration enhancers which can be used in mixture with eucalytpol include, but are not limited to, propylene glycol, N-methyl-2-pyrrolidone, isopropyl myristate and polyethylene glycol. The respective amounts of the eucalyptol and other penetration enhancers in mixture can, of course, vary depending upon the desired effects one wishes to achieve. However, it is generally preferred and convenient that about equivalent amounts, or about a 1:1 mixture of the eucalyptol and additional penetration enhancer, be used.

The concentration of the bio-affecting agent in the formulation can also vary greatly and will be dependent upon many factors, e.g., its type, bioavailability and potency, the condition for which it is administered, the surface area to which it is applied, the type of formulation used and the concentration of eucalyptol in the formulation. Such higher dosages (which may be greater by a factor of 10 to 20 times in the case of an agent such as dexamethasone) can be achieved by increasing the concentration of eucalyptol in the formulation, by increasing the concentration of the drug in the formulation, by increasing the area to which the formulation is applied, or by a combination of these measures. Generally, however, the concentration of the bio-affecting agent will vary from about 0.001% to about 80% of the total composition. The bio-affecting agent may be suspended or dissolved in the eucalyptol-vehicle comprising mixture.

The bio-affecting agents which can be formulated with eucalyptol in accordance with the instant invention are many and generally include any agent whose delivery through the protective outer layer of the skin is desired to be enhanced, e.g., dermally effective dermatological agents and systemically effective therapeutic agents.

Many dermally effective substances are known which can provide beneficial effects when applied topically to the skin, e.g., for the purpose of treating surface or subsurface diseases or for creating skin conditions which protect the skin from external factors. Such dermatological agents which can be made more useful by enhancing their penetration through the protection layer of the skin in accord with the present invention are exemplified by, but not limited to, the following classes of substances:

(a) Antimicrobial substances, such as antibacterial, antifungal, antiacne and antiviral agents. These substances, which can have increased percutaneous absorption when used in the present process, are illustrated by lincomycin; clindamycin; tetracycline, oxytetracycline, chlorotetracycline, and other tetracycline-type antibiotics; erythromycin; 2-thiopyridine N-oxide; halogen compounds, particularly iodine and iodine compounds such as iodine-PVP complex and diiodohydroxyquin; penicillins, such as penicillin G and penicillin V; cephalosporins, i.e. any of the many new forms of these $\beta$-lactam antibiotics such as cephalexin; any of the sulfonamide class of antibacterials; hexachlorophene; chlorhexidine; chloroamine compounds; benzoylperoxide; streptomycin or any other members of the class of aminoglycoside antibiotics; nitrofurantoin, nystatin; amphotericin B; 5-iodo-2-deoxyuridine; griseofulvin; thiabenzadole; and gramicidin. When the level of antimicrobial agents in the skin is greatly increased, the host has an improved ability to combat dermal infections such as boils, infected cuts or incisions, acne, herpes sores and ringworm.

(b) Antimetabolites, for example, 5-fluorouracil, 6-metcaptopurine, mycophenolic acid, methotrexate and the like, which have utility in the treatment of skin cancers and psoriasis.

(c) Anticholinergic agents, which are effective for the inhibition of axillary sweating and for the control of prickly heat. The antiperspirrant activity of agents such as methatropine nitrate, propantheline bromide, scopolamine, methscopolamine bromide, and the new class of soft antiperspirants, quarternary acyloxymethyl ammnonium salts [described, for example, by Bodor et al, J. Med. chem. 23, 474 (1980) and also in United Kingdom Specification No. 2010270, published June 27, 1979] can be greatly enhanced when formulated with eucalyptol.

(d) Steroidal antiinflammatory agents, such as hydrocortisone, hydrocortisone 17-valerate, hydrocortisone 17-butyrate, hydrocortisone 21-acetate, betamethasone valerate, triamcinolone acetonide, fluocinonide, desonide, fluocinolone acetonide, dexamethasone, dexamethasone 21-phosphate, prednisolone, prednisolone 21-phosphate, and haloprednone; as well as non-steroidal antiinflammatory agents, such as indomethacin, naproxen, fenoprofen, ibuprofen, alcolfenac, phenylbutazone, sulindac, desoxysulindac, diflunisal, aspirin and mefenamic acid. These agents are effective for treating inflammatory disorders of the skin and the underlying tissues, and the rate and extent of their penetration can be greatly enhanced by formulation with eucalyptol. Further examples of steroidal antiinflammatory agents for use in the instant compositions include cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone, flumethasone pivalate, flunisolide acetate, fluocortolone, fluorometholone, fluperolone acetate, fluprednisolone, fluprednisolone valerate, meprednisone, methyl prednisolone, paramethasone acetate, prednisolamate, prednisone, prednival, triamcinolone, triamcinolone hexacetonide, cortivazol, formocortal nivazol. Additional non-steroidal antiinflammatory agents which can be formulated in combination with eucalyptol include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamime hydrochloride, dimefadane, indoxole, intrazole, mimbane hydrochloride, paranylene hydrochloride, tetrydamine, benzindopyrine hydrochloide, fluprofen, ibufenac, ketoprofen, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, tramadol and triflumidate.

(e) Local anesthetics, such as benzocaine, procaine, propoxycaine, dibucaine and lidocaine. Such agents are poorly absorbed through the skin but can show enhanced anesthetic properties when formulated with eucalyptol.

(f) Sunscreens, such as p-aminobenzoic acid, p-dimethylaminobenzoic acid, and their alkyl esters. These compounds are poorly retained in the skin but when formulated with eucalyptol can penetrate the stratum corneum and be better retained.

(g) Sex hormones, i.e., the estrogens, androgens and progestins, particularly the natural sex hormones estradiol, testosterone and progesterone, which are useful for a variety of cosmetic purposes such as stimulation of scalp hair growth and use in beauty preparations. Eucalyptol added to these preparations can enhance the penetration of the hormones and increase their retention.

(h) Antihistimines, such as cyproheptadine hydrochlorie (Periactin). These too can be advantageously formulated in combination with eucalyptol.

(i) Miscellaneous dermatological agents, e.g., skin lightening agents such as hydroquinone, keratolytics and agents for treating psoriasis, dermatitis, pruritis and erythema, and emollients.

A wide variety of therapeutic agents is known which can provide beneficial effects when absorbed into the systemic circulation. Formulation of such systemically effective therapeutic agents in combination with eucalyptol can greatly enhance their rate of penetration through the skin and the amount absorbed into the systemic circulation, and thus makes it possible to achieve a systemic effect through topical application of the drug. There is a significant advantage to the topical delivery of systemically effective therapeutic agents in cases where the drug is not absorbed well orally, produces gastric problems, or even if well absorbed, is rapidly metabolized in the liver immediately after absorption (the "first pass" effect). In such cases, by using topical delivery, a systemic response can be elicited at a lower dosage than required orally. At the same time, topical delivery avoids the disadvantages inherent in the intravenous route of administration, which would otherwise be necessary to achieve effective blood levels at reasonable dosage amounts. Such systemically effective therapeutic agents which can be advantageously formulated in combination with eucalyptol are exemplified by, but not limited to, the following classes of substances:

(a) β-Blockers, such as propranolol, bupranolol, metoprolol, nadoxolol, sotalol, alprenolol, oxprenolol, carteolol, labetalol, atenolol, pindolol, timolol and timolol maleate. Because these antiarrhythmic agents are subject to extensive liver metabolism, elevated doses are required orally for clinical efficacy. Thus, formulations of eucalyptol with these agents would be especially advantageous.

(b) Antimicrobial substances, such as antibacterial, antifungal and antiviral agents. These substances, which can have increased percutaneous absorption when used in accord with the present invention, are exemplified by lincomycin; clindamycin; tetracycline, oxtetracycline, chlorotetracycline and other tetracycline-type antibiotics; erythromycin; 2-thiopyridine N-oxide; halogen compounds, especially iodine and iodine compounds; penicillins, such as penicillin G and penicillin V; cephalosporins, i.e., any of the many new forms of these β-lactam antibiotics such as cefalexin and cefoxytin; any of the sulfonamide class of antibacterials; streptomycin or any other members of the class of aminoglycoside antibiotics; nitrofurantoin; nystatin; amphotericin B; 5-iodo-2-deoxyuridine; N-formimidoyl thienamycin monohydrate; 1-ethyl-6-fluoro-1,4-dihydro-4-oxo-7-(1-piperazinyl)-3-quinoline carboxylic acid; phosphonomycin; novabiocin; cycloserine; cephamycins, particularly cephamycin C; and griseofulvin. Eucalyptol formulations of these agents can enhance their delivery through the skin.

(c) Steroidal antiinflammatory agents, i.e., corticosteroids, such as hydrocortisone, hydrocortisone 17-valerate, hydrocortisone 17-butyrate, hydrocortisone 21-acetate, betamethasone valerate, triamcinolone acetonide, flucinonide, desonide, fluocinolone acetonide, dexamethasone, dexamethasone 21-phosphate, prednisolone, prednisolone 21-phosphate, haloprednone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone, flumethasone pivalate, flunisolide acetate, fluocortolone, fluorometholone, fluperolone acetate, fluprednisolone, fluprednisolone valerate, meprednisone, methyl prednisolone, paramethasone acetate, prednisolamate, prednisone, prednival, triamcinolone, triamcinolone hexacetonide, cortivazol, formocortal and nivazol. These compounds, which can be of great value systemically in inflammation, can be better absorbed through the skin when formulated with eucalyptol.

(d) Non-steroidal antiinflammatory agents, such as indomethacin, naproxen, fenoprofen, ibuprofen, alcolfenac, phenylbutazone, mefenamic acid, sulindac, desoxysulindac, diflunisal, aspirin, salicylamide, salicyclic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, ketoprofen, naproxol, fenbufen, cinchophen, diflumidone sodium, fenamole, flutiazin, metazamide, letimide hydrochloride, nexeridine hydrochloride, octazamide, molinazole neocinchophen, nimazole, proxazole citrate, tesicam, tesimide, tolmetin, tramadol and triflumidate. These compounds are effective for treating inflammatory disorders of the skin and the underlying tissues. The rate and extent of penetration of these agents can be greatly enhanced by their formulation with eucalyptol.

(e) Antihypertensives, such as clonidine and α-methyldopa, and antiangina and vasodilator agents such as nitroglycerin, erythritol tetranitrate, isosorbide dinitrate, mannitol hexanitrate, pentaerythrityl tetranitrate, papaverine and dipyridamole. Such agents can have enhanced absorption through the skin when formulated with eucalpytol.

(f) Sex hormones, i.e., the estrogens, androgens and progestins, especially the natural sex hormones estradiol, testosterone and progesterone. These agents show very poor bioavailability by the oral route, but can be well absorbed through the skin when formulated with eucalyptol.

(g) Muscle relaxants, for example cyclobenzaprine hydrochloride and diazepam. These can be advantageously formulated in combination with eucalyptol.

(h) Antiasthma drugs, such as cromoglycic acid and its prodrugs [described, for example, in *International Journal of Pharmaceutics* 7, 63–75 (1980]. Because of its short half-life, cromoglycic acid is an especially desirable candidate for formulation with eucalyptol according to the present invention.

(i) Antiemetics, e.g. pipamazine, chlorpromazine, and dimenhydrinate. These can also be formulated with eucalyptol in accord with the present invention.

In order to further illustrate the present invention and the advantages thereof, the following specific examples are given, it being understood that same are intended only as illustrative and in nowise limitative. In the examples, the effectiveness of eucalyptol as a penetration enhancer is illustrated by measuring the skin penetration of formulations of a number of representative bio-affecting agents with eucalyptol. Also, the skin penetration of bio-affecting agents via eucalyptol formulations were compared with that of other penetration enhancers as well as formulations of bio-affecting agents with common adjuvants. The comparisons made generally consisted of measuring the relative penetration through hairless mouse skin of the various formulations. In every case, those formulations which contained eucalyptol delivered more of the active agent through the skin than did the corresponding commercial preparation.

In the examples, skin penetration was determined using an in vitro diffusion cell procedure. The diffusion cells were obtained from Kersco Engineering Consultants, 3248 Kipling St. Palo Alto, Calif. 94306. The plexiglass diffusion cells consisted of a lower chamber with a side arm to allow sampling of the receptor phase, and a teflon lid. A teflon-coated stirring bar provided efficient mixing. The hairless mice (Jackson Labs) were sacrificed using cervical dislocation and the whole dorsal skin removed. The skin was gently stretched over the lower opening of the teflon lid and secured with a neoprene rubber gasket. The lid was then placed firmly on the lower chamber and secured with three screws. The opening in the lid left exposed an area of 8.0 cm$^2$ (3.2 cm in diameter) on the epidermis side through which penetration was measured. The receptor fluid was 45 mL of buffer consisting of $1.5/10^{-1}M$ NaCl, $5.0\times10^{-4}M$ $NaH_2PO_4$, $2.0\times10^{-4}$ $Na_2HPO_4$ and 200 ppm gentamycin sulfate adjusted to pH 7.2 with sodium hydroxide or hydrochloric acid. Air bubbles were carefully removed from the dermal surface of the skin by tipping the cell. In most cases 100 mg of formulation, solution or suspension containing the drug substance to be tested was applied evenly over the mouse skin. The cell was placed in a thermostated chamber maintained at 32±1° C. and the reservoir stirred by a magnetic stirrer 2.5 Hz. After 24 hours a sample of the receptor fluid was withdrawn by a pipet through the side arm and emptied into a test tube, capped and frozen. The concentration of applied drug in each diffusion cell sample was measured using high pressure liquid chromatography (HPLC). The results reported for each experiment are the average values from three replicate diffusion cells. Chromatography was performed on a high capability chromatograph using assay conditions specific for measurement of the target compounds in each example. Conditions are described in each example.

In the Examples which follow, percents are by weight unless otherwise specified.

EXAMPLE I

The in vitro diffusion cell method described above was used to compare the penetration of procaine in three different solutions of eucalyptol, N,N-diethyl-m-toluamide, and ethanol respectively. The solutions were made 1% in procaine and 10% eucalyptol and N,N-diethyl-m-toluamide in 90% ethanol. The straight ethanol solutions were also 1% in procaine. A 100 μl sample was applied to the hairless mouse skin. Samples were assayed by HPLC using a μBondapak RP cyano column with detection at 254 nm. The mobile phase was 800 mL water, 100 mL tetrahydrofuran, 100 mL acetonitrile and 100 μl ammonium hydroxide.

TABLE I

| | Amount of Procaine Diffused (μg/mL) | | | | | |
|---|---|---|---|---|---|---|
| | Time (Hr.) | | | | | |
| 1% Procaine in | 0.5 | 1 | 2 | 3 | 4 | 5 |
| Eucalyptol/Ethanol (1:9) | 0.7 | 4.0 | 6.8 | 8.7 | 9.1 | 9.4 |
| N,N—Diethyl-m-toluamide/Ethanol (1:9) | 0.0 | 0.1 | 0.6 | 1.1 | 2.2 | 2.1 |
| Ethanol | 0.0 | 0.5 | 2.3 | 4.2 | 5.9 | 6.7 |

EXAMPLE II

The in vitro diffusion cell method described previously was used to compare the penetration of saturated suspensions of procaine in eucalyptol and N,N-diethyl-m-toluamide. The samples were prepared by adding procaine beyond the saturation point to 1 mL of solvent and equilibrating at 32°. A 100 μl sample was applied to the hairless mouse skin. Reservoir samples were analyzed by HPLC as described in Example I.

TABLE II

| | Amount of Procaine Diffused (μg/mL) | | |
|---|---|---|---|
| | Time (Hr.) | | |
| Procaine in | 1 | 6 | 12 |
| Eucalyptol | 7 | 171 | 357 |

TABLE II-continued

| | Amount of Procaine Diffused (μg/mL) | | |
|---|---|---|---|
| | Time (Hr.) | | |
| Procaine in | 1 | 6 | 12 |
| N,N—Diethyl-m-toluamide | 0 | 30 | 153 |

EXAMPLE III

The in vitro diffusion cell method described above was used to compare the penetration of saturated suspensions of bupranolol in eucalyptol, N,N-diethyl-m-toluamide, N-methyl-2-pyrrolidone and propylene glycol. The samples were prepared by adding bupranolol beyond the saturation point to 1 mL of each solvent and equilibrating at 32°. A 100 μl sample was applied to the hairless mouse skin. Reservoir samples were analyzed by HPLC using a μBondapak RP cyano column with detection at 254 nm. The mobile phase was 60% by volume acetonitrile/40% by volume water with 2 mM ammonium dihydrogen phosphate.

TABLE III

| | Amount of Bupranolol Diffused (Total in mg) | | | |
|---|---|---|---|---|
| | Time (Hr.) | | | |
| Bupranolol in | 1 | 2 | 4 | 6 |
| Eucalyptol | 1.79 | 3.13 | 4.06 | 4.82 |
| N,N—Diethyl-m-toluamide | 0.1 | 0.27 | 0.64 | 1.84 |
| N—methyl-2-pyrrolidone | 0.24 | 0.82 | 2.19 | 3.28 |
| Propylene glycol | 0.05 | 0.06 | 0.26 | 1.18 |

EXAMPLE IV

The in vitro diffusion cell method described previously was used to compare the penetration of bupranolol in eucalyptol, N,N-diethyl-m-toluamide, and a 1:1 mixture of the two solvents. The samples were prepared by adding bupranolol beyond the saturation point to 1 mL of each solvent and equilibrating at 32°. A 100 μl sample was applied to the hairless mouse skin. Reservoir samples were analyzed by HPLC as described in Example III.

TABLE IV

| | Amount of Bupranolol Diffused (Total in mg) | | | | |
|---|---|---|---|---|---|
| | Time (Hr.) | | | | |
| Bupranolol in | 1.5 | 3 | 5.5 | 12 | 22 |
| Eucalyptol | 1.64 | 3.45 | 5.34 | 5.49 | 5.97 |
| N,N—Diethyl-m-toluamide | 0 | 0.13 | 0.64 | 4.29 | 10.70 |
| 1:1 mixture | 0.65 | 2.16 | 5.38 | 8.35 | 10.77 |

EXAMPLE V

The in vitro diffusion cell method described previously was used to compare the penetration of saturated suspensions of indomethacin in eucalyptol, N,N-diethyl-m-toluamide (DEET), a 1:1 mixture of eucalyptol and DEET, and a 1:1 mixture of eucalyptol and polyethylene glycol. The samples were prepared by adding indomethacin beyond the saturation point to 1 mL of solvent and equilibrating at 32°. A 100 μl sample was applied to hairless mouse skin. Reservoir samples were analyzed by HPLC using a μBondapak RP cyano column with detection at 254 nm. The mobile phase was 35% by volume acetonitrile/65% by volume water with 2 mM ammonium dihydrogen phosphate.

TABLE V

Amount of Indomethacin Diffused (μg/mL)

| Indomethacin in | Time (Hr.) | | | |
|---|---|---|---|---|
| | 3 | 6 | 12 | 24 |
| Eucalyptol | 4.8 | 11.0 | 30.3 | 43.6 |
| Eucalyptol/DEET 1:1 | 1.8 | 5.0 | 22.6 | 40.5 |
| DEET | 0.1 | 0.5 | 3.5 | 7.1 |
| Eucalyptol/Polyethylene Glycol 1:1 | 4.4 | 8.0 | 17.4 | 24.2 |

EXAMPLE VI

The in vitro diffusion cell method described previously was used to compare the penetration of indomethacin in saturated suspension in propylene glycol, N-methyl-2-pyrrolidone, a 1:1 mixture of eucalyptol and propylene glycol and a 1:1 mixture of eucalyptol and N-methyl-2-pyrrolidone. Conditions used were identical to those described in Example V.

TABLE VI

Amount of Indomethacin Diffused (μg/mL)

| Indomethacin in | Time (Hr.) | | |
|---|---|---|---|
| | 2 | 4 | 24 |
| Propylene Glycol | 0.13 | 0.31 | 3.5 |
| Eucalyptol/Propylene Glycol 1:1 | 5.0 | 7.5 | 23.6 |
| N—Methyl-2-pyrrolidone | 0.29 | 0.86 | 12.0 |
| Eucalyptol/N—Methyl-2-pyrrolidone 1:1 | 6.0 | 4.9 | 27.9 |

EXAMPLE VII

The penetration of dibucaine was compared in saturated suspensions of eucalyptol, a 1:1 mixture of eucalyptol and DEET, isopropyl myristate and a 1:1 mixture of eucalyptol and isopropyl myristate using the previously described diffusion cell method. Samples were prepared as described in Example V and 100 μl applied to hairless mouse skin. Reservoir samples were analyzed by HPLC using a μBondapak RP cyano column with detection at 254 nm. The mobile phase was 50% by volume acetonitrile/50% by volume water with 2 mM ammonium dihydrogen phosphate.

TABLE VII

Amount of Dibucaine Diffused (μg/mL)

| Dibucaine in | Time (Hr.) | | | | |
|---|---|---|---|---|---|
| | 2.5 | 4 | 6 | 12 | 24 |
| Eucalyptol/DEET 1:1 | 3.1 | 9.1 | 12.5 | 35.7 | 71.2 |
| Eucalyptol | 11.0 | 28.7 | 36.4 | 69.1 | 110.1 |
| Isopropyl Myristate | 21.7 | 55.1 | 65.2 | 124.3 | 151.0 |
| Eucalyptol/Isopropyl Myristate 1:1 | 35.3 | 61.8 | 72.9 | 127.6 | 177.8 |

EXAMPLE VIII

The penetration of dibucaine was examined as in Example VIII for saturated suspensions of dibucaine in eucalyptol, propylene glycol, a 1:1 mixture of eucalyptol and DEET, and eucalyptol wherein the set of cells was occluded with Teflon ® discs.

TABLE VIII

Amount of Dibucaine Diffused (μg/mL)

| Dibucaine in | Time (Hr.) | | | |
|---|---|---|---|---|
| | 3 | 6 | 12 | 24 |
| Eucalyptol | 20.6 | 37.2 | 69.2 | 102.4 |
| Eucalyptol (occluded) | 23.2 | 47.9 | 108.7 | 170.0 |

TABLE VIII-continued

Amount of Dibucaine Diffused (μg/mL)

| Dibucaine in | Time (Hr.) | | | |
|---|---|---|---|---|
| | 3 | 6 | 12 | 24 |
| Eucalyptol/DEET 1:1 | 8.1 | 17.4 | 42.3 | 85.8 |
| Propylene Glycol | 2.3 | 7.4 | 26.8 | 44.4 |

EXAMPLE IX

The diffusion of dibucaine was examined as described in Example V for saturated suspensions of the dibucaine in N-methyl-2-pyrrolidone, a 1:1 mixture of eucalyptol and N-methyl-2-pyrrolidone, propylene glycol and polyethylene glycol respectively.

TABLE IX

Amount of Dibucaine Diffused (μg/mL)

| Dibucaine in | Time (Hr.) | | | | |
|---|---|---|---|---|---|
| | 2.5 | 4 | 6 | 12 | 24 |
| N—Methyl-2-pyrrolidone | 4.0 | 8.3 | 13.3 | 36.3 | 73.0 |
| Eucalyptol/N—methyl-2-pyrrolidone 1:1 | 8.7 | 18.7 | 25.7 | 62.7 | 104.3 |
| Eucalyptol/propylene glycol 1:1 | 7.5 | 19.0 | 24.7 | 82.3 | 117.0 |
| Eucalyptol/polyethylene glycol 400 1:1 | 6.0 | 12.0 | 16.0 | 41.0 | 89.3 |

EXAMPLE X

The in vitro diffusion cell method described previously was used to compare the penetration of benzocaine via saturated suspensions of isopropyl myristate and 1:1 mixtures of eucalyptol and isopropyl myristate, polyethylene glycol and propylene glycol. Samples were prepared as described in previous examples and 100 μl samples were applied to hairless mouse skin. Reservoir samples were analyzed by HPLC using a μBondapak RP cyano column with detection at 254 nm. The mobile phase was 25% by volume tetrahydrofuran/75% by volume water.

TABLE X

Amount of Benzocaine Diffused (μg/mL)

| Benzocaine in | Time (Hr.) | | | | |
|---|---|---|---|---|---|
| | 2 | 4 | 6 | 12 | 24 |
| Isopropyl Myristate | 30.0 | 126.7 | 156.7 | 316.7 | 376.7 |
| Eucalyptol/Isopropyl Myristate 1:1 | 33.3 | 133.3 | 163.3 | 343.3 | 450.0 |
| Eucalyptol/Polyethylene glycol 400 1:1 | 40.0 | 143.3 | 220.0 | 430.0 | 620.0 |
| Eucalyptol/Propylene glycol 1:1 | 26.7 | 160.0 | 213.3 | 306.7 | 400.0 |

EXAMPLE XI

The diffusion of benzocaine was examined as in Example X for saturated suspensions of benzocaine in eucalyptol, propylene glycol, a 1:1 mixture of eucalyptol and DEET, and eucalyptol wherein the set of cells was occluded with Teflon ® discs.

TABLE XI

Amount of Benzocaine Diffused (μg/mL)

| Benzocaine in | Time (Hr.) | | | | |
|---|---|---|---|---|---|
| | 2 | 4 | 6 | 12 | 24 |
| Eucalyptol | 100.0 | 103.3 | 106.7 | 110.0 | 123.3 |
| Eucalyptol (occluded) | 86.7 | 140.0 | 233.3 | 416.7 | 486.7 |

TABLE XI-continued

| | Amount of Benzocaine Diffused (μg/mL) | | | | |
| --- | --- | --- | --- | --- | --- |
| | Time (Hr.) | | | | |
| Benzocaine in | 2 | 4 | 6 | 12 | 24 |
| Eucalyptol/DEET 1:1 | 42.2 | 26.7 | 36.7 | 66.7 | 140.0 |
| Propylene glycol | 16.7 | 36.7 | 60.0 | 143.3 | 193.3 |

EXAMPLE XII

The previously described in vitro diffusion cell method was used to compare the penetrations of bupranolol octyl sulfate, a lipophilic salt of the beta-blocker bupranolol. Saturated solutions of bupranolol octyl sulfate in polyethylene glycol 400 and a 1:1 mixture of eucalyptol and polyethylene glycol 400 were used. The procedure of Example III was followed.

TABLE XII

| | Amount of Bupranolol diffused (μg/mL) | | |
| --- | --- | --- | --- |
| | Time (Hr.) | | |
| Bupranolol octyl sulfate in | 3 | 6 | 24 |
| Polyethylene Glycol 400 | 0.05 | 0.10 | 1.50 |
| Eucalyptol/Polyethylene glycol 400 1:1 | 2.40 | 17.80 | 135.3 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What I claim is:

1. A composition of matter for topical application comprising from 0.001% to about 80% of the total composition of a systemically or dermally effective non-steroidal anti-inflammatory agent selected from the group consisting of indomethacin, naproxen, fenoprofen, ibuprofen, sulindac and desoxysulindac and a skin permeation enhancing amount of eucalyptol.

2. A composition as defined by claim 1 further comprising a non-toxic topical carrier.

3. A composition as defined by claim 2 wherein the concentration of the eucalyptol is at least 0.1% of the carrier.

4. A composition as defined by claim 1 wherein said bio-affecting agent is indomethacin.

5. A composition as defined by claim 1, wherein said bio-affecting agent is ibuprofen.

6. A composition of matter as defined by claim 2, formulated as a solution, suspension, lotion, cream, ointment or aerosol spray.

7. A composition as defined by claim 1, further comprising a penetration enhancer in mixture with the eucalyptol.

8. A composition as defined by claim 7, wherein the penetration enhancer is selected from the group consisting of N,N-diethyl-m-toluamide, polyethylene glycol, propylene glycol, N-methyl-2-pyrrolidone and isopropyl myristate.

9. A composition as defined by claim 7, comprising a mixture of N-N-diethyl-m-toluamide and eucalyptol.

10. A composition as defined by claim 7, 8 or 9, wherein said mixture is a 1:1 mixture.

11. A method for eliciting a dermatological or systemic therapeutic response in a mammal which comprises topically administering thereto a dermally effective or systemically effective amount of a composition as defined by claim 1.

* * * * *